United States Patent [19]

Pfister

[11] 4,217,361

[45] Aug. 12, 1980

[54] DISUBSTITUTED XANTHONE-2-CARBOXYLIC ACID ANTIALLERGY AGENTS

[75] Inventor: Jurg R. Pfister, Los Altos, Calif.

[73] Assignee: Syntex (U.S.A.) Inc., Palo Alto, Calif.

[21] Appl. No.: 908,312

[22] Filed: May 22, 1978

[51] Int. Cl.$^2$ .................... C07D 311/86; A61K 31/35
[52] U.S. Cl. ............................. 424/283; 260/335
[58] Field of Search ..................... 260/335; 424/283

[56] References Cited

U.S. PATENT DOCUMENTS

| | | | |
|---|---|---|---|
| 3,706,768 | 12/1972 | Bays | 260/335 |
| 3,886,181 | 5/1975 | Pfister et al. | 260/335 |
| 3,963,752 | 6/1976 | Pfister et al. | 260/335 |
| 3,963,753 | 6/1976 | Pfister et al. | 260/335 |
| 3,988,352 | 10/1976 | Pfister et al. | 260/335 |

*Primary Examiner*—Norma S. Milestone
*Attorney, Agent, or Firm*—Alan M. Krubiner; Tom M. Moran

[57] ABSTRACT

Compositions containing and methods employing, as the essential ingredient, novel substituted xanthone-2-carboxylic acid compounds which are useful in the treatment of allergic conditions. Methods for preparing these compounds and compositions and intermediates therein are also disclosed.

11 Claims, No Drawings

DISUBSTITUTED XANTHONE-2-CARBOXYLIC ACID ANTIALLERGY AGENTS

FIELD OF THE INVENTION

The present invention is directed to novel substituted xanthone carboxylic acid compounds and to compositions containing and methods utilizing these compounds as the essential ingredient in the treatment of symptoms associated with allergic manifestations, for example, asthmatic conditions.

In a first aspect of the present invention, novel 5,7-xanthone-2-carboxylic acids selected from those represented by the following formulas:

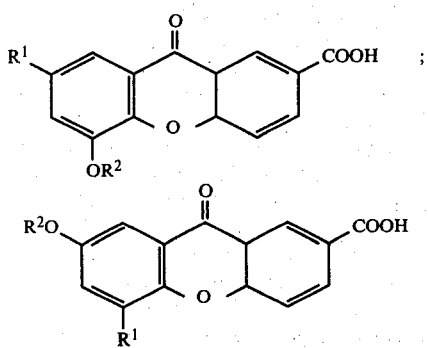

and pharmaceutically acceptable, non-toxic esters, amides and salts thereof, wherein $R^1$ is $R(O)_nS—$ where R is $C_1$ to $C_6$ linear or branched alkyl or $C_4$ to $C_7$ cyclic alkyl optionally substituted with $C_1$ to $C_4$ linear or branched alkyl and n is the integer 0, 1 or 2 or $RC(O)—$ where R is as previously defined and $R^2$ is $C_2$ to $C_6$ linear or branched hydroxyalkyl or hydroxy-substituted $C_4$ to $C_7$ cyclic alkyl optionally substituted with $C_1$ to $C_4$ linear or branched alkyl. Thus included within the scope of the present invention are the following subgeneric compounds of the formulas (I) and (II) described below.

1. The 5,7-substituted xanthone-2-carboxylic acid compounds of the following formula:

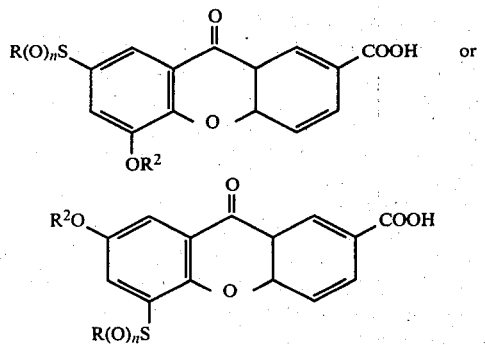

and the pharmaceutically acceptable, non-toxic esters, amides and salts thereof where R is $C_1$ to $C_6$ linear or branched alkyl or $C_4$ to $C_6$ cyclic alkyl optionally substituted with $C_1$ to $C_4$ linear or branched alkyl, n is the integer 0, 1 or 2 and $R^2$ is $C_2$ to $C_6$ linear or branched hydroxyalkyl or hydroxy-substituted $C_4$ to $C_7$ cyclic alkyl optionally substituted with $C_1$ to $C_4$ linear or branched alkyl.

Preferred compounds of formulas (I)a and (II)a are those bearing the $R(O)_nS—$ substitutent where n is the integer 1 or 2 R is $C_1$ to $C_4$ linear or branched alkyl and the $R^2$ substituent selected from linear or branched alkyl of the formula $C_xH_{2x}OH$ or $C_xH_{2x-1}(OH)_2$ where x is the integer 2 to 6 and cyclic alkyl of the formula $C_yH_{2y-2}OH$ or $C_yH_{2y-3}(OH)_2$ where y is the integer 4 to 6.

Particularly preferred compounds of formulas (I)a and (II)a are those bearing the $R(O)_nS—$ substituent where n is the integer 2 and R is selected from the group methyl, ethyl, n-propyl, isopropyl and tert-butyl and the $R^2$ substituent is selected from 2-hydroxyethyl, 3-hydroxy-n-propyl, 2-methyl-2hydroxyethyl, 4-hydroxy-n-butyl, 3-hydroxy-n-butyl, 2-hydroxy-n-butyl, 2-hydroxycyclopentyl, 3-hydroxycyclopentyl, 2-methyl-3-hydroxycyclopentyl, 3,4-dihydroxycyclopentyl, 4-hydroxycyclohexyl and 3,4-dihydroxycyclohexyl and, 2. The 5,7-substituted xanthone-2-carboxylic acid compounds of the formula:

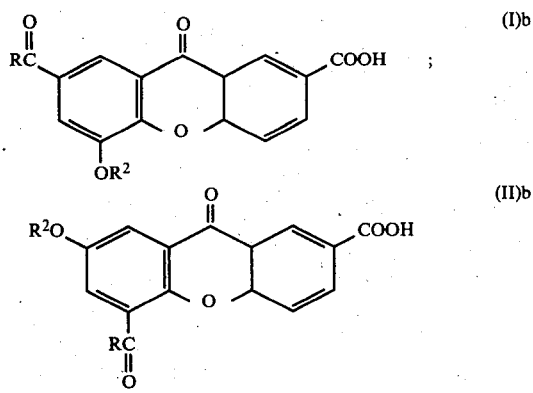

and pharmaceutically acceptable, non-toxic esters, amides and salts thereof where R is $C_1$ to $C_6$ linear or branched alkyl or $C_4$ to $C_7$ cyclic alkyl optionally substituted with $C_1$ to $C_4$ linear or branched alkyl and $R^2$ is $C_2$ to $C_6$ linear or branched hydroxyalkyl or hydroxy-substituted $C_4$ to $C_7$ cyclic alkyl optionally substituted with $C_1$ to $C_4$ linear or branched alkyl.

Preferred compounds of formulas (I)b and (II)b are those wherein R is selected from the group $C_1$ to $C_4$ linear or branched alkyl and cyclohexyl or cyclopentyl optionally substituted with $C_1$ to $C_4$ linear or branched alkyl and $R^2$ is selected from the group linear or branched alkyl of the formula $C_xH_{2x}OH$ or $C_xH_{2x-1}(OH)_2$ where x is the integer 2 to 6 and cyclic alkyl of the formula $C_yH_{2y-2}OH$ or $C_yH_{2y-3}(OH)_2$ where y is the integer 4 to 7.

Particularly preferred compounds of formulas (I)b and (II)b are those wherein R is selected from the group methyl, ethyl, n-propyl, iso-propyl and tert-butyl and where $R^2$ is selected from the group 2-hydroxyethyl, 3-hydroxy-n-propyl, 2-methyl-2-hydroxyethyl, 4-hydroxy-n-butyl, 3-hydroxy-n-butyl, 2-hydroxy-n-butyl, 2-hydroxycyclopentyl, 3-hydroxycyclopentyl, 2-methyl-3-hydroxycyclopentyl, 3,4-dihydroxycyclopentyl, 4-hydroxycyclohexyl and 3,4-dihydroxycyclohexyl.

In a second aspect, the present invention is directed to a method useful for relieving symptoms associated with allergic manifestations such as are brought about by antigen-antibody (allergic) reactions. In the relief of these symptoms, the method hereof serves to inhibit the effects of the allergic reaction when administered in an effective amount. While not intending to be bound by any theoretical mechanism of action, the method hereof is believed to operate by inhibiting the release and/or the action of toxic products, e.g., histamine, 5-hydroxytryptamine, slow releasing substance of anaphylaxis (SRS-A), and others which are produced as a result of a combination of specific antibody-antigen (allergic) reaction. These properties make the subject compounds particularly useful in the treatment of various allergic conditions.

The second aspect of the present invention thus relates to a method useful for inhibiting the effects of the allergic reaction which comprises administering an effective amount of a compound selected from those represented by the following formulas:

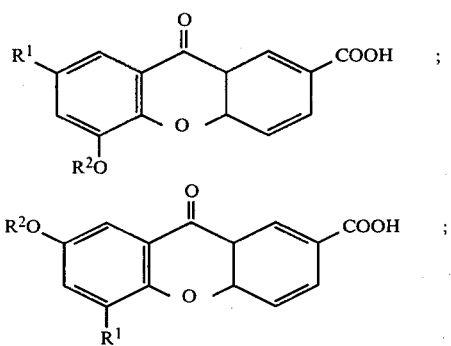

and pharmaceutically acceptable, non-toxic esters, amides, and salts thereof where $R^1$ is $R(O)_nS—$ where R is $C_1$ to $C_6$ linear or branched alkyl or $C_4$ to $C_7$ cyclic alkyl optionally substituted with $C_1$ to $C_4$ linear or branched alkyl and n is the integer 0, 1 or 2 or RC(O)— where R is as previously defined and $R^2$ is $C_2$ to $C_6$ linear or branched hydroxyalkyl or hydroxy-substituted $C_4$ to $C_7$ cyclic alkyl optionally substituted with $C_1$ to $C_4$ linear or branched alkyl or a pharmaceutically acceptable, non-toxic composition incorporating said acids, esters, amides or salts as an essential ingredient.

The compounds of the present invention are also smooth muscle relaxants, e.g., bronchial dilators, and are therefore useful in the treatment of conditions in which such agents may be indicated, as for instance in the treatment of bronchioconstriction. The compounds of the present invention are also vasodilators and are therefore useful in the treatment of conditions in which such agents may be indicated, as for instance in renal and cardiac disorders.

The present invention, in a third aspect, is directed to pharmaceutical compositions useful for inhibiting the effects of the allergic reaction comprising an effective amount of a compound selected from those represented by the formula:

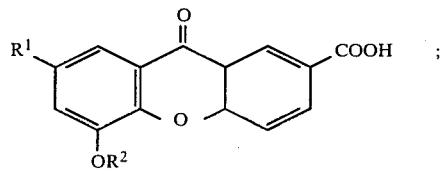

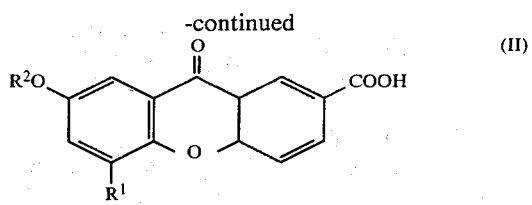

and pharmaceutically acceptable non-toxic esters, amides and salts thereof where $R^1$ is $R(O)_nS—$ where R is $C_1$ to $C_6$ linear or branched alkyl or $C_4$ to $C_7$ cyclic alkyl optionally substituted with $C_1$ to $C_4$ linear or branched alkyl and n is the integer 0, 1 or 2 or RC(O)— where R is as previously defined and $R^2$ is $C_2$ to $C_6$ linear or branched hydroxyalkyl or hydroxy-substituted $C_4$ to $C_7$ cyclic alkyl optionally substituted with $C_1$ to $C_4$ linear or branched alkyl, in admixture with a pharmaceutically acceptable non-toxic carrier.

In the practice of the method of the present invention, an effective amount of a compound of the present invention or pharmaceutical compositions thereof, as defined above, is administered via any of the usual and acceptable methods known in the art, either singly or in combination with another compound or compounds of the present invention or other pharmaceutical agents, such as antibiotics, hormonal agents, and so forth. These compounds or compositions can thus be administered orally, topically, parenterally, or by inhalation and in the form of either solid, liquid, or gaseous dosage including tablets, suspensions, and aerosols, as discussed in more detail hereinafter. The administration can be conducted in single unit dosage form with continuous therapy or in single dose therapy ad libitum. In the preferred embodiments, the method of the present invention is practiced on humans when relief of symptoms is specifically required, or, perhaps, imminent; however, the method hereof is also usefully practiced as continuous or prophylactic treatment.

In view of the foregoing as well as in consideration of the degree of severity of the condition being treated, age of subject, and so forth, all of which factors being determined by routine experimentation by one skilled in the art, the effective dosage in accordance herewith can vary over a wide range. Generally, an effective amount ranges from about 0.005 to about 100 mg. per kg. of body weight per day and preferably from about 0.01 to about 100 mg. per kg. of body weight per day. In alternate terms, an effective amount in accordance herewith generally ranges from about 0.5 to about 7000 mg. per day per subject.

Useful pharmaceutical carriers for the preparation of the compositions hereof, can be solids, liquids, or gases. Thus, the compositions can take the form of tablets, pills, capsules, powders, sustained release formulations, solutions, suspensions, elixirs, aerosols, and the like. The carrier can be selected from the various oils including those of petroleum, animal, vegetable, or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical excipients include starch, cellulose, talc, glucose, lactose, sucrose, gelatin, malt, rice, flour, chalk, silica gel, magnesium stearate, sodium stearate, glyceryl monostearate, sodium chloride, dried skim milk, glycerol, propylene glycol, water, ethanol, and the like. Suitable pharmaceutical carriers and their formulation are described in "Remingtons Pharmaceutical Sciences" by E. W. Martin. Such compositions will, in any event, contain an effective amount of the active compound of the present invention together with a suitable amount of carrier so as to prepare the proper dosage form for proper administration to the host.

The compounds of the present invention demonstrate activity as inhibitors of the effects of the allergic reaction as measured by tests indicative of such activity involving passive cutaneous anaphylaxis as substantially described, for example, by J. Goose et al., Immunology, 16,749 (1969).

A more detailed description of the preparation of the various xanthones of use in the method and compositions of the present invention can be had by reference to U.S. Pat. No. 3,706,768, filed Nov. 17, 1970, U.S. Pat. No. 3,801,598, filed Aug. 23, 1971, U.S. Pat. No. 3,849,568, filed Jan. 12, 1972, U.S. Pat. No. 3,821,251, filed Jan. 12, 1972, those procedures described by J. R. Pfister in U.S. application Ser. No. 884,456 filed Mar. 8, 1978, U.S. Pat. No. 3,873,714, filed Jan. 12, 1972, U.S. Pat. No. 3,886,181, filed May, 5, 1975, U.S. Pat. No. 3,818,042 filed June 5, 1972, and U.S. Pat. No. 3,885,108, filed May 17, 1972. The above cited U.S. patents and U.S. patent application are incorporated herein by reference.

The compounds of the present invention of formulas (I) and (II) where n is the integer 0 are synthesized by condensing a 5-hydroxy-7-$R^1$- or 5-$R^1$-7-hydroxyxanthone-2-carboxylic acid with a hydroxylalkyl halide, preferably a hydroxyalkyl bromide in the presence of base such as potassium carbonate or sodium hydroxide in an organic inert solvent such as ethanol. The reaction is conducted at temperatures ranging from about 20° to about 80° C. for a time sufficient to complete the reaction, from about 8 to about 48 hours.

The compounds of the present invention of formulas (I) and (II) where n is the integer 1 or 2 are prepared from the compounds of the present invention of formulas (I) and (II) where n is the integer 0 by an oxidation reaction. Thus, the compounds of formulas (I) and (II) where n is the integer 0 can be oxidized with a peracid, such as peracetic acid, m-chloroperbenzoic acid, p-nitroperbenzoic acid, perphthalic acid, and the like, to give compounds of the present invention of formulas (I) and (II) when n is the integer 1 or 2. The oxidation is preferably conducted in a liquid reaction medium such as a chlorinated hydrocarbon, e.g., chloroform, methylene chloride or carbon tetrachloride. The reaction is conducted at temperatures ranging from about 0° to about 60° C., preferably from about 20° to about 30° C. and for a period of time sufficient to complete the reaction, ranging from about 1 hour to about 6 hours. In the preferred embodiment, the reaction is conducted by employing from about 1 to about 1.1 moles of peracid for every mole of compound of formulas (I) and (II) where n is the integer 0.

Alternatively, the compounds of the present invention of formulas (I) and (II) when n is the integer 0 are oxidized with excess hydrogen peroxide to give the aforesaid compounds where n is the integer 1 or 2. The peroxide oxidation is preferably conducted in a liquid reaction medium such as a lower carboxylic acid, e.g., acetic acid or propionic acid. The reaction is further conducted at temperatures ranging from about 20° to about 100° C., preferably from 80° to about 90° C. and for a period of time sufficient to complete the reaction, ranging from about 30 minutes to about 3 hours. In the preferred embodiments, the reaction is conducted employing from about 5 to about 10 moles of hydrogen peroxide per mole of compounds of formulas (I) and (II) where n is the integer 0.

In the oxidation steps, and particularly that employing a peracid, a mixture of products of formulas (I) and (II), where n is the integer 1 and where n is the integer 2 may be obtained. These mixtures can be conventionally separated, such as via chromatography, if desired, to isolate the oxidized products.

The acid esters of the xanthone-2-carboxylic acids hereof are preferably prepared by reaction with the desired $C_1$ to $C_6$ linear or branched alkanol in the presence of acid catalyst by conventional esterification methods.

The amides of the xanthone-2-carboxylic acids are prepared by treatment of the carboxylic acids with thionyl chloride followed by reaction with the appropriate amine or ammonia, i.e., anhydrous ammonia or the $C_1$ to $C_6$ linear or branched alkyl or di-$C_1$ to $C_6$ linear or branched alkylamine. In the alkyl sulfinyl series (compounds (I) and (II) where n is the integer 1) the carboxylic acid amides are preferably prepared at the corresponding $C_1$ to $C_6$ linear or branched alkylthio stage [compounds (I)a and (II)a when n is the integer 0] followed by oxidation thereof, as described above.

The salts of the xanthone-2-carboxylic acids hereof are prepared by treating the corresponding carboxylic acids with a pharmaceutically acceptable base. Representative salts derived from such pharmaceutically acceptable base include the sodium, potassium, lithium, ammonia, calcium, magnesium, ferrous, ferric, zinc, manganous, aluminum, manganic, trimethylamine, triethylamine, tripropylamine, beta-dimethylaminoethanol, triethanolamine, betadiethylaminoethanol, arginine, lysine, histidine, N-ethylpiperidine, hydrabamine, choline, betaine, ethylenediamine, glucosamine, methyl glucamine, theobromine, purines, piperazine, piperidine, polyamine resins, caffeine or procaine salts. The compounds of formulas (I) and (II) treated with the dialkanolamines $(HO)_z(CH_2)_y$—NH—$(CH_2)_{y'}(OH)_{z'}$ where y and y' are the same or different and are the integer 0 or 1, most preferably diethanolamine, are preferred. y And y' may be linear or branched $C_1$ to $C_6$ carbon atoms. The reaction is conducted in an aqueous solution, alone or in combination with an inert, water miscible organic solvent, at a temperature of from about 0° to about 100° C., preferably at room temperature. Typical inert, water miscible organic solvents include methanol, ethanol, isopropanol, butanol, acetone, dioxane or tetrahydrofuran. In a similar manner, by replacing the hydrogen atom of the aforesaid dialkanolamine with the group —$(CH_2)_xOH$, where x is the integer 2 to 6, N,N-substituted amino-$C_2$ to $C_6$ alkyl carboxylates are prepared. When divalent metal salts are prepared, such as the calcium salts or magnesium salts of the acids, the free acid starting material is treated with about a one half molar equivalent of a pharmaceutically acceptable base. When the aluminum salts of the acids are prepared, about one third molar equivalent of the pharmaceutically acceptable base is employed.

In the preferred embodiment of the present invention, the calcium salts and magnesium salts of the acids are prepared by treating the corresponding sodium or potassium salts with at least one half molar equivalent of calcium chloride or magnesium chloride, respectively, in an aqueous solution, alone or in combination with an inert water miscible organic solvent, at a temperature of from about 20° to about 100° C.

In the preferred embodiment of the present invention, the aluminum salts of the acids are prepared by treating the acids with at least one third molar equivalent of an aluminum alkoxide, such as aluminum triethoxide, aluminum tripropoxide, and the like, in a hydrocarbon solvent, such as benzene, xylene, cyclohexane, and the like at a temperature of from about 20° to about 115° C.

In the present specification and claims, the term "$C_1$ to $C_6$ linear or branched alkyl" is intended to mean an alkyl group containing between 1 and 6 carbon atoms including straight and branched chains, for example, methyl, ethyl, n-propyl, isopropyl, n-butyl, and the like. Similarly, "$C_1$ to $C_4$ linear or branched alkyl" is intended to mean those alkyl groups containing between 1 and 4 carbon atoms including both straight and branched chains. By the term "$C_2$ to $C_6$ linear or branched hydroxyalkyl" is meant alkyl groups of 2 to 6 carbon atoms in length and having substituted thereon one or two hydroxy groups. These include both straight and branched chains and are for example, hydroxyethyl, 2-hydroxy-n-propyl, 2-hydroxy-n-butyl, 2-hydroxymethyl-1-propyl, 2,3-dihydroxy-n-propyl, and the like. By the term "hydroxy-substituted $C_4$ to $C_7$ cyclic alkyl optionally substituted with $C_1$ to $C_4$ linear branched alkyl" is meant those cyclic alkyl groups having 4 to 7 carbon atoms either in a fully saturated ring or substituted on such ring and additionally having one or two hydroxy substituents and are illustrated by, for example, the groups 3-hydroxycyclobutyl, 3-hydroxycyclopentyl, 3,4-dihydroxycyclopentyl, 2-methyl-3-hydroxycyclopentyl, 2-ethyl-3-hydroxycyclopentyl, 4-hydroxycyclohexyl and the like.

By the term "pharmaceutically acceptable, non toxic esters and amides" is respectively intended to mean those esters and amides containing $C_1$ to $C_6$ linear or branched alkyl groups as defined above as well as mono-$C_1$ to $C_6$ linear or branched alkyl or di-$C_1$ to $C_6$ linear or branched alkyl-substituted amide groups. The alkyl group in the case of the $C_1$ to $C_6$ linear or branched alkyl esters can additionally have attached one or two di-$C_1$ to $C_6$ linear or branched alkylamino groups. The alkyl groups on the amide may also have a hydroxy group attached thereto. Examples of such esters include ethyl, n-propyl, n-butyl, 3-(N,N-dimethyl)-1-propionate, 3-(N,N-dimethyl)-1-butyl and the like. The amides are illustrated by the following groups attached to the nitrogen atom of the amide: methyl, ethyl, n-propyl, n-butyl, dimethyl, diethyl, di-n-propyl, methylethyl, 2-hydroxyethyl, di-(2-hydroxyethyl) and the like.

Some of the compounds of the present invention possess assymetric centers. As such, these compounds exist in their d- or l- forms. Unless otherwise noted, all assymetric center-containing compounds have been isolated as racemic mixtures (dl).

EXAMPLE 1

Preparation of the compounds of formulas (I)a and (II)a and (I)b and (II)b when n is the integer 0 can be accomplished by the following general procedure.

(a) A mixture of 10 mmol of a 7-(or 5-) substituted 5-(or 7-) hydroxyxanthone-2-carboxylic alkyl ester, 25 mmol of the requisite haloalkanol, 3.45 g (25 mmol) dry potassium carbonate and 100 ml dimethylformamide is stirred at room temperature until thin layer chromatography indicates the absence of starting material. Water (300 ml) is then added and the resulting precipitate is filtered off, washed with water, dried, and recrystallized from chloroform/ethanol.

(b) 10 Mmol of the ester of (a) is refluxed with 800 mg (20 mmol) sodium hydroxide in 100 ml 80% aqueous ethanol for 30 minutes. The solution is acidified with dilute acetic acid, cooled, and the crystalline product isolated by suction filtration. The compounds (the free xanthone-2-carboxylic acids) can be recrystallized from aqueous acetic acid.

Prepared in this manner using 2-bromo-1-ethanol are the following illustrative compounds:

5-(2-hydroxyethoxy)-7-acetylxanthone-2-carboxylic acid;

5-(2-hydroxyethoxy)-7-n-propionylxanthone-2-carboxylic acid;

5-(2-hydroxyethoxy)-7-n-butyroylxanthone-2-carboxylic acid;

5-(2-hydroxyethoxy)-7-methylthioxanthone-2-carboxylic acid, m.p. 262°, methyl ester, m.p. 223°–225°;

5-(2-hydroxyethoxy)-7-ethylthioxanthone-2-carboxylic acid;

5-(2-hydroxyethoxy)-7-n-propylthioxanthone-2-carboxylic acid;

5-acetyl-7-(2-hydroxyethoxy)-xanthone-2-carboxylic acid, m.p. 287°–288°, ethyl ester, m.p. 191°;

5-propionyl-7-(2-hydroxyethoxy)-xanthone-2-carboxylic acid;

5-n-butyroyl-7-(2-hydroxyethoxy)-xanthone-2-carboxylic acid;

5-methylthio-7-(2-hydroxyethoxy)-xanthone-2-carboxylic acid, m.p. 290–291°, ethyl ester, m.p. 220–221°;

5-ethylthio-7-(2-hydroxyethoxy)-xanthone-2-carboxylic acid; and 5-n-propylthio-7-(2-hydroxyethoxy)-xanthone-2-carboxylic acid.

EXAMPLE 2

Preparation of the compounds of formulas (I)a and (II)a where n is the integer 1.

A mixture of 0.01 mol of the 7-(or 5-) (hydroxyalkylthio)-xanthone-2-carboxylic acid of Example 1, 1.53 ml (0.011 mol), triethylamine and 100 ml 50% aqueous methanol is warmed to 65° C. with stirring until a clear solution results. After cooling to 25° C., 3.75 ml (0.033 mol) 30% hydrogen peroxide ($H_2O_2$) is added, and stirring is continued at 25° C. for 3 days. The solution is then acidified with 2N HCl, treated with sodium bisulfite ($NaHSO_3$), and concentrated in vacuum. The product is washed with water and recrystallized from acetic acid (AcOH). By this technique, the following compounds are prepared:

5-(2-hydroxyethoxy)-7-methylsulfinylxanthone-2-carboxylic acid, m.p. 272°–274°, ethyl ester 193°–194°;

5-(2-hydroxyethoxy)-7-ethylsulfinylxanthone-2-carboxylic acid;

5-(2-hydroxyethoxy)-7-n-propylsulfinylxanthone-2-carboxylic acid;

5-methylsulfinyl-7-(2-hydroxyethoxy) carboxylic acid;

5-ethylsulfinyl-7-(2-hydroxyethoxy)-xanthone-2-carboxylic acid; and 5-n-propylsulfinyl-7-(2-hydroxyethoxy)-xanthone-2-carboxylic acid.

EXAMPLE 3

Preparation of the compounds of the present invention of formulas (I)a and (II)a where n is the integer 2.

A mixture of 0.01 mol of the 7(or 5-)-hydroxyalkyl-thio)-xanthone-2-carboxylic acid of Example 1, 11.3 ml (0.1 mol) 30% $H_2O_2$, and 120 ml AcOH is refluxed for 90 minutes. The hot solution is diluted with 150 ml water and cooled. The crystals thus formed are filtered off, washed with water and recrystallized from AcOH. By this procedure, the following compounds are prepared:

5-(2-hydroxyethoxy)-7-methylsulfonylxanthone-2-carboxylic acid, m.p. 330°, ethyl ester, 237°–239°;
5-(2-hydroxyethoxy)-7-ethylsulfonylxanthone-2-carboxylic acid;
5-(2-hydroxyethoxy)-7-n-propylsulfonylxanthone-2-carboxylic acid;
5-methylsulfonyl-7-(2-hydroxyethoxy)-xanthone-2-carboxylic acid, m.p. 271°–273°, ethyl ester m.p. 247°;
5-ethylsulfonyl-7-(2-hydroxyethoxy)-xanthone-2-carboxylic acid; and
5-n-propylsulfonyl-7-(2-hydroxyethoxy)-xanthone-2-carboxylic acid.

What is claimed is:

1. A compound selected from the group represented by

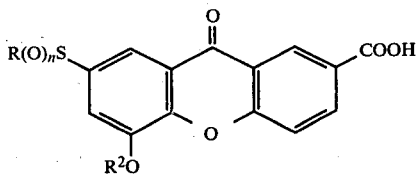   (I)a

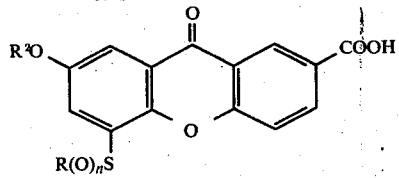   (II)a and the pharmaceutically acceptable, non-toxic esters, amides and salts thereof wherein R is $C_1$ to $C_6$ linear or branched alkyl or $C_4$ to $C_6$ cyclic alkyl optionallly substituted with $C_1$ to $C_4$ linear or branched alkyl, n is the integer 1 or 2 and $R^2$ is $C_2$ to $C_6$ linear or branched hydroxy alkyl or hydroxy-substituted $C_4$ to $C_7$ cyclic alkyl optionally substituted with $C_1$ to $C_4$ linear or branched alkyl.

2. The compound according to claim 1 of formula (I)a.

3. The compound according to claim 2 wherein n is the integer 2, R is $C_1$ to $C_4$ linear or branched alkyl and $R^2$ is selected from the group linear or branched alkyl of the formula $C_xH_{2x}OH$ or $C_xH_{2x-1}(OH)_2$ and cyclic alkyl of the formula $C_yH_{2y-2}OH$ or $C_yH_{2y-3}(OH)_2$ where y is the integer 4 to 6 and x is the integer 2 to 6.

4. The compound according to claim 2 wherein R is selected from the group methyl, ethyl, n-propyl, isopropyl and tert-butyl and $R^2$ is selected from the group 2-hydroxyethyl, 3-hydroxy-n-propyl, 2-methyl-2-hydroxyethyl, 4-hydroxy-n-butyl, 3-hydroxy-n-butyl, 2-hydroxy-n-butyl, 2-hydroxycyclopentyl, 3,4-dihydroxycyclopentyl, 4-hydroxycyclohexyl and 3,4-dihydroxycyclohexyl.

5. The compound according to claim 4 where R is isopropyl and $R^2$ is 2-hydroxyethyl.

6. The compound according to claim 1 of the formula (II)a.

7. The compound according to claim 6 wherein n is the integer 2, R is $C_1$ to $C_4$ linear or branched alkyl and $R^2$ is selected from the group linear or branched alkyl of the formula $C_xH_{2x}OH$ or $C_xH_{2x-1}(OH)_2$ and cyclic alkyl of the formula $C_yH_{2y-2}OH$ or $C_yH_{2y-3}(OH)_2$ where y is the integer 4 to 6 and X is the integer 2 to 6.

8. The compound according to claim 7 wherein R is selected from the group methyl, ethyl, n-propyl, isopropyl and tert-butyl and $R^2$ is selected from the group 2-hydroxyethyl, 3-hydroxy-n-propyl, 2-methyl-2-hydroxyethyl, 4-hydroxy-n-butyl, 3-hydroxy-n-butyl, 2-hydroxy-n-butyl, 2-hydroxycyclopentyl, 3,4-dihydroxycyclopentyl, 4-hydroxycyclohexyl and 3,4-dihydroxycyclohexyl.

9. The compound according to claim 8 where R is isopropyl and $R^2$ is 2-hydroxyethyl.

10. A method for inhibiting the effects of allergic reactions which comprises administering an effective amount of a compound selected from the group represented by

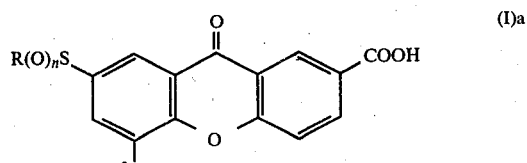   (I)a

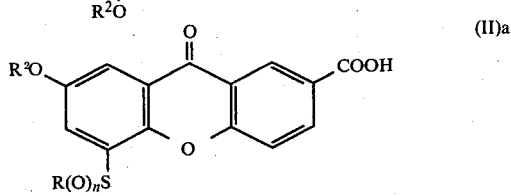   (II)a and the pharmaceutically acceptable, non-toxic esters, amides and salts thereof wherein R is $C_1$ to $C_6$ linear or branched alkyl or $C_4$ to $C_6$ cyclic alkyl optionally substituted with $C_1$ to $C_4$ linear or branched alkyl, n is the integer 1 or 2 and $R^2$ is $C_2$ to $C_6$ linear or branched hydroxy alkyl or hydroxy-substituted $C_4$ to $C_7$ cyclic alkyl optionally substituted with $C_1$ to $C_4$ linear or branched alkyl in admixture with a pharmaceutically acceptable, non-toxic carrier.

11. A composition useful for inhibiting the effects of allergic reactions which comprises an effective amount of a compound selected from the group represented by

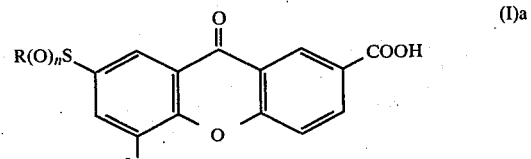   (I)a

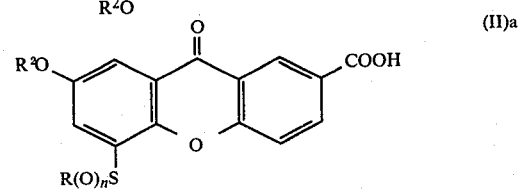   (II)a and the pharmaceutically acceptable, non-toxic esters, amides and salts thereof wherein R is $C_1$ to $C_6$ linear or branched alkyl or $C_4$ to $C_6$ cyclic alkyl optionally substituted with $C_1$ to $C_4$ linear or branched alkyl, n is the integer 1 or 2 and $R^2$ is $C_2$ to $C_6$ linear or branched hydroxy alkyl or hydroxy-substituted $C_4$ to $C_7$ cyclic alkyl optionally substituted with $C_1$ to $C_4$ linear or branched alkyl in admixture with a pharmaceutically acceptable, non-toxic carrier.

* * * * *